United States Patent [19]

Bays et al.

[11] Patent Number: 4,585,781
[45] Date of Patent: Apr. 29, 1986

[54] HETEROCYCLIC DERIVATIVES

[75] Inventors: David Bays; Roger Hayes; Philip Blatcher, all of Hertfordshire, United Kingdom

[73] Assignee: Glaxo Group Limited, London, England

[21] Appl. No.: 567,005

[22] Filed: Dec. 30, 1983

[30] Foreign Application Priority Data

Dec. 31, 1982 [GB] United Kingdom ............... 8237069
Mar. 24, 1983 [GB] United Kingdom ............... 8308171

[51] Int. Cl.$^4$ ............... C07D 403/12; C07D 417/12;
A61K 31/425; A61K 31/415
[52] U.S. Cl. ............... 514/370; 514/381;
548/193; 548/198; 548/251
[58] Field of Search ............... 548/193, 198, 251;
514/370, 381

[56] References Cited

FOREIGN PATENT DOCUMENTS

| 30092 | 6/1981 | European Pat. Off. |
| 60696 | 9/1982 | European Pat. Off. |
| 60697 | 9/1982 | European Pat. Off. |
| 2082584 | 3/1982 | United Kingdom ............... 548/251 |
| 2125404 | 3/1984 | United Kingdom ............... 548/193 |

Primary Examiner—Robert Gerstl
Attorney, Agent, or Firm—Bacon & Thomas

[57] ABSTRACT

This invention relates to compounds of the general formula (I)

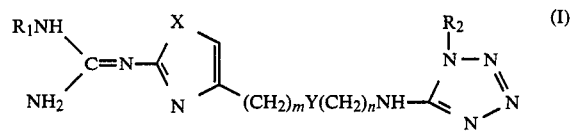

and physiologically acceptable salts and hydrates thereof, in which $R_1$ represents a hydrogen atom or an alkyl, alkanoyl, aroyl or trifluoroalkyl group;

$R_2$ represents a hydrogen atom or an alkyl or alkenyl group or $C_{2-6}$ alkyl group substituted by a hydroxy or alkoxy group;

X represents a sulphur atom or NH;
Y represents an oxygen or sulphur atom or a bond;
m represents 1, 2 or 3; and
n represents 2, 3 or 4.

The compounds show pharmacological activity as selective histamine $H_2$-antagonists.

7 Claims, No Drawings

HETEROCYCLIC DERIVATIVES

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds which are more particularly described below, for example show inhibition of the secretion of gastric acid when this is stimulated via histamine receptors (Ash and Schild, Brit. J. Pharmacol. Chemother. 1966, 27, 427). Their ability to do so can be demonstrated in the perfused rat stomach using the method described in British Patent Specification No. 1,565,966, modified by the use of sodium pentobarbitone (50 mg/kg) as anaesthetic instead of urethane, and in conscious dogs equipped with Heidenhain pouches using the method described by Black et al Nature 1972 236, 385. Furthermore, the compounds antagonise the effect of histamine on the contraction frequency of isolated guinea pig right atrium. Certain compounds according to the invention have the advantage of an extended duration of action.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator. Thus, they may be used for example, either alone, or in combination with other active ingredients in the treatment of allergic and inflammatory conditions of the skin.

The present invention provides compounds of the general formula (I)

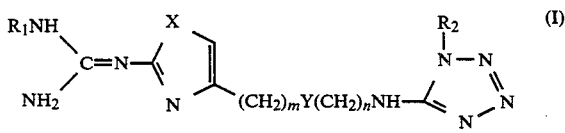

and physiologically acceptable salts and hydrates thereof, in which
$R_1$ represents a hydrogen atom or an alkyl, alkanoyl, aroyl or trifluoroalkyl group;
$R_2$ represents a hydrogen atom or an alkyl or alkenyl group or $C_{2-6}$ alkyl group substituted by a hydroxy or alkoxy group,
X represents a sulphur atom or NH;
Y represents an oxygen or sulphur atom or a bond;
m represents 1, 2 or 3; and
n represents 2, 3 or 4.

In the above formula (I) the term 'alkyl' as a group or part of a group means that the group is straight or branched and, unless otherwise stated, contains 1 to 6 carbon atoms, and in particular 1 to 4 carbon atoms, e.g. methyl or ethyl, and the term 'alkenyl' means that the group has preferably 3 to 6 carbon atoms. The term 'aryl' as a group or part of a group preferably means phenyl or substituted phenyl, for example phenyl substituted with one or more $C_{1-3}$ alkyl or $C_{1-3}$ alkoxy groups, or halogen atoms, e.g. fluorine.

According to one aspect the invention relates to compounds of formula (I) in which $R_1$ is other than a trifluoroalkyl group.

The following are examples of suitable meanings for the groups $R_1$ and $R_2$:
$R_1$ may be for example a hydrogen atom or a methyl, ethyl, propyl, isopropyl, butyl, acetyl, propionyl, benzoyl or 2,2,2-trifluoroethyl group.
$R_2$ may be for example a methyl, ethyl, propyl, allyl, 2-hydroxyethyl or 2-methoxyethyl group.
Examples of suitable chains $—(CH_2)_mY(CH_2)_n—$ are $—CH_2S(CH_2)_2—$, $—CH_2O(CH_2)_3—$ and $—(CH_2)_4—$.
Within the definition of formula (I)
$R_1$ is preferably a hydrogen atom;
$R_2$ is preferably a hydrogen atom, a $C_{1-4}$ alkyl group (e.g. methyl) or a $C_{2-6}$ alkyl group substituted by a hydroxy group (e.g. 2-hydroxyethyl).
X is preferably a sulphur atom;
Y is preferably a sulphur atom;
m is preferably 1;
n is preferably 2.

Particularly preferred compounds according to the invention are
N-[4-[[[2-[(1-methyl-1H-tetrazol-5-yl)amino]ethyl]thio]methyl]-2-thiazolyl]guanidine, and physiologically acceptable salts thereof; and
N-[4-[[[2-[[1-(2-hydroxyethyl)-1H-tetrazol-5-yl]amino]ethyl]thio]methyl]-2-thiazolyl]guanidine, and physiologically acceptable salts thereof.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The present invention also extends to bioprecursors of the compounds of formula (I). Bioprecursors are compounds which have a structure different to that of the compounds of formula (I) but which, upon administration to the animal or human being are converted in the body into a compound of formula (I).

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention is 1 to 4 doses to a total of 5 mg to 1 g per day, preferably 5 to 500 mg per day, dependent upon the condition of the patient.

It will be appreciated that in the methods for the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_2$ is an alkyl group bearing a hydroxy substituent. Standard protection and deprotection procedures can be employed, for examples amines may be protected by formation of a phthalimide group which may subsequently be cleaved by treatment with a hydrazine, e.g. hydrazine hydrate or a primary amine, for example methylamine. Hydroxyl groups may for example be protected by formation of ethers e.g. tetrahydropyranyl, or esters of carboxylic acids such as alkanoic acid, e.g. acetic acid, which may subsequently be removed by hydrolysis.

In describing the processes which may be used for preparing the compounds of formula (I) or intermediates useful in the preparation thereof, any of $R_1$, $R_2$, Alk, X, Y, Z, n and m in the various formulae are as defined in formula (I) unless otherwise stated.

Compounds of formula (I) may be prepared by reacting an amine of formula (II)

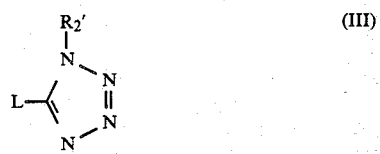
(II)

preferably in the form of a salt, e.g. a hydrochloride, with a tetrazole of formula (III)

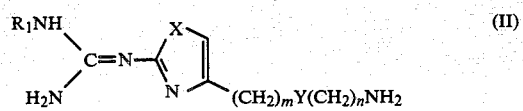
(III)

where L is a leaving group such as halogen, e.g. bromine, and $R_2'$ is the group $R_2$ or a group convertible thereto. The reaction is preferably carried out with heating, for example within the range 80° to 200° C, in the absence or presence of a solvent such as an alkanol, e.g. butanol, optionally in a sealed vessel and preferably in the presence of a base such as triethylamine.

The compounds of formula (II) may be prepared as described in British Patent Specification No. 2001624A. The tetrazoles of formula (III) in which L represents a leaving group such as halogen are either known compounds or may be prepared by methods analogous to those described in British Patent Specification No. 1364917 and G. B. Barlin, J. Chem. Soc., (B), 1967, 641, e.g. by halogenation e.g. bromination of a compound of formula (IV)

(IV)

Tetrazoles of formula (IV) are either known compounds or, when $R_2$ is a hydroxyalkyl group or a group convertible thereto, may be prepared by reaction of a corresponding 2-aminoalkanol derivative $NH_2$—$R_2$ with sodium azide and triethylorthoformate in the presence of a solvent such as acetic acid.

Compounds of formula (III) in which L is a leaving group such as halogen, e.g. bromine or chlorine and $R_2'$ is the group $CH_2CH_2OR_3$ where $R_3$ is a hydrogen atom or a hydroxyl protecting group, e.g. tetrahydropyranyl ether, are novel compounds and represent a further aspect of the present invention.

Where the product of any one of the above processes is a free base and an acid addition salt, in particlar a physiologically acceptable salt is required, the salt may be formed in conventional manner. Thus, for example, a generally convenient method of forming the salts is to mix appropriate quantities of the free base and the acid in an appropriate solvent(s) e.g. an alcohol such as ethanol or an ester such as ethyl acetate. The invention also includes interconversion of one salt of the compound of formula (I) into another.

The invention is illustrated but not limited by the following Examples and Preparations, in which temperatures are in °C.

PREPARATION 1

1H-Tetrazole-1-ethanol acetate (ester)

2-Aminoethanol acetate (ester) hydrochloride (4.19 g), sodium azide (2.34 g), triethylorthoformate (6.67 g) and acetic acid (6 ml) were stirred at 70° for 24 h. The mixture was cooled and acidified to pH 1 with concentrated hydrochloric acid. After 2 h, excess saturated potassium carbonate solution was added and the mixture was extracted with ethyl acetate to give the title compound (4 g) as a pale yellow oil.

N.m.r. (DMSO): 0.49, s, (1H); 5.23, s, (2H); 5.57, t, (2H); 8.00, s, (3H).

PREPARATION 2

5-Bromo-1H-tetrazole-1-ethanol acetate (ester)

Bromine (69.1 g) in chloroform (80 ml) was added to a stirred refluxing solution of 1H-tetrazole-1-ethanol acetate (ester) (33.8 g) in acetic acid (200 ml) and chloroform (400 ml). After 72 h the mixture was cooled and evaporated, excess, saturated potassium carbonate solution was added and the mixture was extracted with ethyl acetate to give the title compound (48.2 g) as a cream solid, m.p. 55°-6° (from diethyl ether).

PREPARATION 3

5-Bromo-1H-tetrazole-1-ethanol

5-Bromo-1H-tetrazole-1-ethanol acetate (ester) (40 g) and 2N hydrochloric acid (216 ml) were stirred at room temperature for 22 h.

The solution was concentrated to ca. 75 ml and basified with excess solid potassium carbonate. Any solid present was dissolved by the addition of water and the solution was extracted with ethyl acetate.

The combined extracts were dried and evaporated to give a yellow oil which solidifed. Recrystallisation from isopropyl gave the title compound (24.7 g) as a white solid m.p. 73°-4°.

PREPARATION 4

5-Bromo-1-[2-[(tetrahydro-2H-pyran-2-yl)oxy]ethyl]-1H-tetrazole

A suspension of 5-bromo-1H-tetrazole-1-ethanol (5.79 g) and pyridinium 4-toluenesulphonate (0.5 g) in dichloromethane (50 ml) and dihydropyran (4 ml) was stirred at room temperature for 16 h to give a colourless solution. Water (25 ml) and sodium carbonate solution (25 ml) were added, the phases were separated and the aqueous phase was extracted with dichloromethane. The combined extracts were washed with water and brine, dried and evaporated to give the title compound (6.5 g) as a colourless oil.

Assay Found: C, 35.1; H, 4.81; N, 20.0; $C_8H_{13}BrN_4O_2$ requires: C, 34.7; H, 4.73; N, 20.2%.

EXAMPLE 1

N-[4-[[[2-[(1-Methyl-1H-tetrazol-5-yl)amino]ethyl]thio]methyl]-2-thiazolyl]guanidine A solution of N-[4-[[(2-aminoethyl)thio]methyl]-2-thiazolyl]guanidine dihydrochloride (1.53 g) and triethylamine (2.5 ml) in n-butanol (45 ml) was stirred at 20° for 0.5 hours and then 5-bromo-1-methyl-1H-tetrazole (0.82 g) was added. The mixture was heated at reflux for 24 hours and the solvent removed in vacuo. The dark brown residue was partitioned between ethyl acetate and aqueous sodium carbonate. The ethyl acetate extract was washed with brine and evaporated to leave a brown gum which was chromatographed on silica using methanol: ammonia (250:1) to give a dark brown gum (0.6 g). This gum was chroamtographed on alumina using dichloromethane: ethanol:0.88 ammonia (100:8:1) to give a brown solid (0.16 g) which was crystallised from acetone to give the title compound (0.038 g) as a cream white solid m.p. 80-3°.

N.m.r. (CD$_3$OD): 3.46, s, (1H); 6.25, s, (3H); 6.32, s, (2H); 6.44, t, (2H); 7.23, t, (2H).

EXAMPLE 2

N-[4-[[[2-[[1-(2-Hydroxyethyl)-1H-tetrazol-5-yl]amino]ethyl]thio]methyl]-2-thiazolyl]guanidine, d, l-tartarate A solution of N-[4-[[(2-aminoethyl)thio]methyl]-2-thiazolyl]guanidine, dihydrochloride (1.3 g) and triethylamine (1.3 ml) in butan-1-ol (10 ml) was stirred under nitrogen for 1 h, and 5-bromo-1-[2-[tetrahydro-2H-pyran-2-yl]oxy]ethyl]-1H-tetrazole (1.2 g) in butan-1-ol (5 ml) was added. The reaction solution was gently refluxed for 26 h and evaporated in vacuo to leave a black solid residue which was chromatographed on a column of alumina using dichloromethane:ethanol:ammonia—(150:8:1), to give a brown gum. This was dissolved in dilute hydrochloric acid, stirred for 2 h at room temperature and washed with diethyl ether. The pH of the aqueous phase was adjusted to pH 8 with sodium carbonate and extracted with diethyl ether. The organic extract was dried (MgSO$_4$) and evaporated to leave a light brown foam. This foam was chromatographed on a column of silica using dichloromethane:ethanol:ammonia—(50:8:1) to give a colourless gum (0.1 g) which was dissolved in absolute ethanol and added to a solution of d, l-tartaric acid in absolute ethanol. The resulting solution was stirred for 2 h and dry diethyl ether was added to precipitate the title compound (0.105 g) as a white hygroscopic solid m.p. 60°-65°.

N.m.r. (D$_2$O): 3.00, s, (1H); 5.62, s, (2H); 5.72, t, (2H); 6.06, t, (2H); 6.20, s, (2H); 6.52, t, (2H); 7.15, t, (2H).

Examples of Pharmaceutical Compositions

Tablets

|  | mg/tablet |
| --- | --- |
| Active ingredient | 20.0 |
| Microcrystalline Cellulose USP | 178.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the compression weight and using punches to suit.

The tablets may be film coated with suitable film forming materials, such as hydroxypropyl methylcellulose, using standard techniques. Alternatively the tablets may be sugar coated.

Injection for Intravenous Administration

|  | % w/v |
| --- | --- |
| Active ingredient | 0.2 |
| Sodium Chloride BP | as required |
| Water for Injection BP to | 100.00 |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or another suitable gas.

We claim:

1. A compound of formula (I)

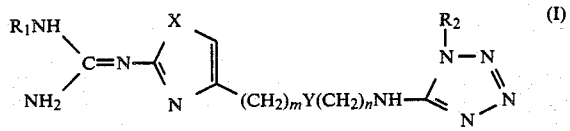

or a physiologically acceptable salt or hydrate thereof, in which $R_1$ represents a hydrogen atom or a $C_{1-6}$ alkyl, $C_{2-7}$ alkanoyl, aroyl or trifluoro $C_{1-6}$ alkyl group;

$R_2$ represents a hydrogen atom or a $C_{1-6}$ alkyl or $C_{3-6}$ alkenyl group or $C_{2-6}$ alkyl group substituted by a hydroxy or $C_{1-6}$ alkoxy group;

X represents a sulphur atom or NH;

Y represents an oxygen or sulphur atom or a bond;

m represents 1, 2 or 3;

n represents 2, 3 or 4; and aryl as part of a group represents phenyl or phenyl substituted with one or more $C_{1-3}$ alkyl or $C_{1-3}$ alkoxy groups or halogen atoms.

2. A compound as claimed in claim 1, in which $R_1$ is a hydrogen atom or a methyl, ethyl, propyl, isopropyl, butyl, acetyl, propionyl, benzoyl or 2,2,2-trifluoroethyl group; and $R_2$ is a methyl, ethyl, propyl, allyl, 2-hydroxyethyl or 2-methoxyethyl group.

3. A compound as claimed in claim 1 in which the chain $—(CH_2)_mY(CH_2)_n—$ is $—CH_2S(CH_2)_2—$, $—CH_2O(CH_2)_3$ or $—(CH_2)_4—$.

4. A compound as claimed in claim 1 in which:

$R_1$ is a hydrogen atom;

$R_2$ is a hydrogen atom, a $C_{1-4}$ alkyl group or a $C_{2-6}$ alkyl group substituted by a hydroxy group;

X is a sulphur atom;

Y is a sulphur atom;

m is 1;

n is 2.

5. A compound as claimed in claim 1, which is N-[4-[[[2-[(1-methyl-1H-tetrazol-5-yl)amino]ethyl]thio]methyl]-2-thiazolyl]guanidine or a physiologically acceptable salt thereof; or N-[4-[[[2-[[1-(2-hydroxyethyl)-1H-tetrazol-5-yl]amino]ethyl]thio]methyl]-2-thiazolyl]guanidine or a physiologically acceptable salt thereof.

6. A pharmaceutical composition for the treatment of conditions mediated through histamine $H_2$-receptors which comprises an effective amount of a compound as claimed in claim 1 together with at least one inert pharmaceutically acceptable carrier or diluent.

7. A method of treating a condition mediated through histamine $H_2$-receptors which comprises administering to a patient an effective amount of a compound as defined in claim 1 to relieve said condition.

* * * * *